(12) United States Patent
Linhardt et al.

(10) Patent No.: US 7,837,934 B2
(45) Date of Patent: Nov. 23, 2010

(54) PACKAGING SOLUTIONS

(75) Inventors: Jeffrey G. Linhardt, Fairport, NY (US); Jay F. Kunzler, Canandaigua, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 12/258,916

(22) Filed: Oct. 27, 2008

(65) Prior Publication Data

US 2009/0173044 A1    Jul. 9, 2009

Related U.S. Application Data

(60) Provisional application No. 61/019,868, filed on Jan. 9, 2008.

(51) Int. Cl.
A61L 12/08 (2006.01)

(52) U.S. Cl. .................. 422/28; 422/292; 514/840

(58) Field of Classification Search ................. None
See application file for complete search history.

(56) References Cited

U.S. PATENT DOCUMENTS

| | | |
|---|---|---|
| 3,408,429 A | 10/1968 | Wichterle |
| 3,660,545 A | 5/1972 | Wichterle |
| 4,113,224 A | 9/1978 | Clark et al. |
| 4,136,250 A | 1/1979 | Mueller et al. |
| 4,153,641 A | 5/1979 | Deichert et al. |
| 4,197,266 A | 4/1980 | Clark et al. |
| 4,555,732 A | 11/1985 | Tuhro |
| 4,740,533 A | 4/1988 | Su et al. |
| 4,910,277 A | 3/1990 | Bambury et al. |
| 4,954,587 A | 9/1990 | Mueller |
| 5,010,141 A | 4/1991 | Mueller |
| 5,034,461 A | 7/1991 | Lai et al. |
| 5,070,215 A | 12/1991 | Bambury et al. |
| 5,079,319 A | 1/1992 | Mueller |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Künzler et al. |
| 5,358,995 A | 10/1994 | Lai et al. |
| 5,387,662 A | 2/1995 | Künzler et al. |
| 5,449,729 A | 9/1995 | Lai |
| 5,500,144 A | 3/1996 | Potini et al. |
| 5,512,205 A | 4/1996 | Lai |
| 5,532,224 A * | 7/1996 | Desai et al. .............. 514/63 |
| 5,604,189 A | 2/1997 | Zhang et al. |
| 5,607,908 A | 3/1997 | Potini et al. |
| 5,610,252 A | 3/1997 | Bambury et al. |
| 5,616,757 A | 4/1997 | Bambury |
| 5,708,094 A | 1/1998 | Lai et al. |
| 5,710,302 A | 1/1998 | Künzler et al. |
| 5,714,557 A | 2/1998 | Künzler et al. |
| 5,739,371 A * | 4/1998 | O'Lenick, Jr. .............. 556/418 |
| 5,773,396 A | 6/1998 | Zhang et al. |
| 5,882,687 A | 3/1999 | Park et al. |
| 5,908,906 A | 6/1999 | Künzler et al. |
| 6,440,366 B1 | 8/2002 | Salpekar et al. |
| 6,531,432 B2 | 3/2003 | Molock et al. |
| 2003/0109390 A1 | 6/2003 | Salpekar et al. |
| 2006/0047006 A1 | 3/2006 | Salamone et al. |
| 2007/0149428 A1* | 6/2007 | Ammon et al. .............. 510/112 |

FOREIGN PATENT DOCUMENTS

| | | |
|---|---|---|
| WO | WO 96/31792 | 10/1996 |
| WO | WO9720019 | 6/1997 |

OTHER PUBLICATIONS

Lai, Yu-Chin, "The Role of Bulky Polysiloxanylalkyl Methacryates in Polyurethane-Polysiloxane Hydrogels" *Journal of Applied Polymer Science*, vol. 60, 1193-1199 (1996).

* cited by examiner

*Primary Examiner*—Elizabeth L McKane
(74) *Attorney, Agent, or Firm*—Glenn D. Smith (57) ABSTRACT

Packaging systems for storing ophthalmic devices such as contact lenses and to methods for packaging such ophthalmic devices with solutions to improve the comfort of the lenses during wear are disclosed. A packaging system includes an ophthalmic device stored in an aqueous packaging solution comprising a substantially water-soluble silicone-containing surfactant. Such solutions are retained on the surface of an unused lens for extended periods of time, resulting in surface modification that persists in the eye, which may provide significant improvement in the wetting properties of fresh contact lenses used for the first time and, moreover, even several hours after lens insertion, preventing dryness and improving lubricity.

20 Claims, 2 Drawing Sheets

PACKAGING SOLUTIONS

This application claims the benefit of Provisional Patent Application No. 61/019,868 filed Jan. 9, 2008 which is incorporated by reference herein.

BACKGROUND OF THE INVENTION

1. Technical Field

The present invention generally relates to packaging solutions for ophthalmic devices such as contact lenses.

2. Description of Related Art

Blister-packs and glass vials are typically used to individually package each soft contact lens for sale to a customer. Saline or deionized water is commonly used to store the lens in the blister-packs, as mentioned in various patents related to the packaging or manufacturing of contact lenses. Because lens material may tend to stick to itself and to the lens package, packaging solutions for blister-packs have sometimes been formulated to reduce or eliminate lens folding and sticking. For this reason, polyvinyl alcohol (PVA) has been used in contact-lens packaging solutions.

It has been stated that if a lens is thoroughly cleaned before insertion, lacrimal fluid can adequately wet the lens. Furthermore, the difficulties of adding a surfactant to a packaging solution, including the possibility of lowering shelf-life and/or adverse reactions during heat sterilization, have further limited the use of surfactants in a packaging solution for the purpose of providing any possible or marginal effect on lens comfort. It is only after a lens has been worn, when proteins or other deposits have formed on the surface of the lens, that surfactants have been used in standard lens-care solutions.

It is highly desirable that a contact lens be as comfortable as possible for wearers. Manufacturers of contact lenses are continually working to improve the comfort of the lenses. Nevertheless, many people who wear contact lenses still experience dryness or eye irritation throughout the day and particularly towards the end of the day. An insufficiently wetted lens at any point in time will cause significant discomfort to the lens wearer. Although wetting drops can be used as needed to alleviate such discomfort, it would certainly be desirable if such discomfort did not arise in the first place.

U.S. Pat. No. 6,440,366 ("the '366 patent") discloses a package containing a contact lens suitable for immediate use which comprises (a) a solution comprising a non-ionic surfactant that is a compound comprising at least 90 weight percent of poly(oxyethylene) and poly(oxypropylene) segments, in one or more block copolymer chains, and (b) an effective amount of a tonicity adjusting agent such that the solution has an osmolality of 200 to 400 mOsm/kg; wherein the solution has a pH of about 6 to 8 and is heat sterilized and lacks an effective disinfecting amount of a disinfecting agent. The '366 patent further discloses that the surfactant is a poly(oxypropylene)-poly(oxyethylene) adduct of ethylene diamine.

It would be desirable to provide an improved packaging system for ophthalmic devices such as a contact lens such that the lens would be comfortable to wear in actual use following its removal from the packaging system and allow for extended wear of the lens without irritation or other adverse effects to the cornea.

SUMMARY OF THE INVENTION

In accordance with one embodiment of the present invention, a method of preparing a package comprising a storable, sterile ophthalmic device is provided comprising:

(a) immersing an ophthalmic device in an aqueous packaging solution comprising a substantially water-soluble silicone-containing surfactant, wherein the solution has an osmolality of at least about 200 mOsm/kg and a pH in the range of about 6 to about 9;

(b) packaging the solution and the ophthalmic device in a manner preventing contamination of the device by microorganisms; and (c) sterilizing the packaged solution and ophthalmic device.

In accordance with a second embodiment of the present invention, a packaging system for the storage of an ophthalmic device is provided comprising a sealed container containing one or more unused ophthalmic devices immersed in an aqueous packaging solution comprising a substantially water-soluble silicone-containing surfactant, wherein the solution has an osmolality of at least about 200 mOsm/kg, a pH of about 6 to about 9 and is heat sterilized.

In accordance with a third embodiment of the present invention, a packaging system for the storage of an ophthalmic device is provided comprising:

(a) an aqueous packaging solution comprising a substantially water-soluble silicone-containing surfactant, wherein the solution has an osmolality of at least about 200 mOsm/kg and a pH in the range of about 6 to about 9;

(b) at least one ophthalmic device; and (c) a container for holding the solution and ophthalmic device sufficient to preserve the sterility of the solution and ophthalmic device, wherein the solution does not contain an effective disinfecting amount of a disinfecting agent.

The aqueous packaging solutions of the present invention containing at least a substantially water-soluble silicone-containing surfactant advantageously provide a more uniform coating on the surface of an ophthalmic device such as a contact lens thereby resulting in improved lubricity of the lens. Thus, the lens will be more comfortable to wear in actual use and would allow for the extended wear of the lens without irritation or other adverse effects to the cornea. For example, contact lenses treated with the aqueous packaging solution of the present invention containing at least a substantially water-soluble silicone-containing surfactant were manually inspected and found to be more lubricious than a contact lens not treated with the aqueous packaging solution of the present invention. Accordingly, contact lenses can have an improved coefficient of friction after being treated with an aqueous packaging solution of the present invention containing at least a substantially water-soluble silicone-containing surfactant as compared to contact lenses treated with an aqueous packaging solution in the absence of a substantially water-soluble silicone-containing surfactant.

DETAILED DESCRIPTION OF THE PREFERRED EMBODIMENTS

The present invention provides a packaging system for the storage of ophthalmic devices intended for direct contact with body tissue or body fluid. As used herein, the term "ophthalmic device" refers to devices that reside in or on the eye.

These devices can provide optical correction, wound care, drug delivery, diagnostic functionality or cosmetic enhancement or effect or a combination of these properties. Representative examples of such devices include, but are not limited to, soft contact lenses, e.g., a soft, hydrogel lens; soft, non-hydrogel lens and the like, hard contact lenses, e.g., a hard, gas permeable lens material and the like, intraocular lenses, overlay lenses, ocular inserts, optical inserts and the like. As is understood by one skilled in the art, a lens is considered to be "soft" if it can be folded back upon itself without breaking.

The ophthalmic devices can be any material known in the art capable of forming an ophthalmic device including a contact lens. In one embodiment, an ophthalmic device includes devices which are formed from material not hydrophilic per se. Such devices are formed from materials known in the art and include, by way of example, polysiloxanes, perfluoropolyethers, fluorinated poly(meth)acrylates or equivalent fluorinated polymers derived, e.g., from other polymerizable carboxylic acids, polyalkyl(meth)acrylates or equivalent alkylester polymers derived from other polymerizable carboxylic acids, or fluorinated polyolefins, such as fluorinated ethylene propylene polymers, or tetrafluoroethylene, preferably in combination with a dioxol, e.g., perfluoro-2,2-dimethyl-1,3-dioxol. Representative examples of suitable bulk materials include, but are not limited to, Lotrafilcon A, Neofocon, Pasifocon, Telefocon, Silafocon, Fluorsilfocon, Paflufocon, Silafocon, Elastofilcon, Fluorofocon or Teflon AF materials, such as Teflon AF 1600 or Teflon AF 2400 which are copolymers of about 63 to about 73 mol % of perfluoro-2,2-dimethyl-1,3-dioxol and about 37 to about 27 mol % of tetrafluoroethylene, or of about 80 to about 90 mol % of perfluoro-2,2-dimethyl-1,3-dioxol and about 20 to about 10 mol % of tetrafluoroethylene.

In another embodiment, an ophthalmic device includes devices which are formed from material hydrophilic per se, since reactive groups, e.g., carboxy, carbamoyl, sulfate, sulfonate, phosphate, amine, ammonium or hydroxy groups, are inherently present in the material and therefore also at the surface of an ophthalmic device manufactured therefrom. Such devices are formed from materials known in the art and include, by way of example, polyhydroxyethyl acrylate, polyhydroxyethyl methacrylate (HEMA), polyvinyl pyrrolidone (PVP), polyacrylic acid, polymethacrylic acid, polyacrylamide, polydimethylacrylamide (DMA), polyvinyl alcohol and the like and copolymers thereof, e.g., from two or more monomers selected from hydroxyethyl acrylate, hydroxyethyl methacrylate, N-vinyl pyrrolidone, acrylic acid, methacrylic acid, acrylamide, dimethyl acrylamide, vinyl alcohol and the like. Representative examples of suitable bulk materials include, but are not limited to, Polymacon, Tefilcon, Methafilcon, Deltafilcon, Bufilcon, Phemfilcon, Ocufilcon, Focofilcon, Etafilcon, Hefilcon, Vifilcon, Tetrafilcon, Perfilcon, Droxifilcon, Dimefilcon, Isofilcon, Mafilcon, Nelfilcon, Atlafilcon and the like. Examples of other suitable bulk materials include balafilcon A, hilafilcon A, alphafilcon A, bilafilcon B and the like.

In another embodiment, ophthalmic devices include devices which are formed from material which are amphiphilic segmented copolymers containing at least one hydrophobic segment and at least one hydrophilic segment which are linked through a bond or a bridge member.

It is particularly useful to employ biocompatible materials herein including both soft and rigid materials commonly used for ophthalmic lenses, including contact lenses. In general, non-hydrogel materials are hydrophobic polymeric materials that do not contain water in their equilibrium state. Typical non-hydrogel materials comprise silicone acrylics, such as those formed bulky silicone monomer (e.g., tris(trimethylsiloxy)silylpropyl methacrylate, commonly known as "TRIS" monomer), methacrylate end-capped poly(dimethylsiloxane) prepolymer, or silicones having fluoroalkyl side groups (polysiloxanes are also commonly known as silicone polymers).

Hydrogels in general are a well-known class of materials that comprise hydrated, crosslinked polymeric systems containing water in an equilibrium state. Accordingly, hydrogels are copolymers prepared from hydrophilic monomers. In the case of silicone hydrogels, the hydrogel copolymers are generally prepared by polymerizing a mixture containing at least one device-forming silicone-containing monomer and at least one device-forming hydrophilic monomer. Either the silicone-containing monomer or the hydrophilic monomer can function as a crosslinking agent (a crosslinker being defined as a monomer having multiple polymerizable functionalities) or a separate crosslinker may be employed. Silicone hydrogels typically have a water content between about 10 to about 80 weight percent.

Representative examples of useful hydrophilic monomers include, but are not limited to, amides such as N,N-dimethylacrylamide and N,N-dimethylmethacrylamide; cyclic lactams such as N-vinyl-2-pyrrolidone; and (meth)acrylated poly(alkene glycols), such as poly(diethylene glycols) of varying chain length containing monomethacrylate or dimethacrylate end caps. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277, the disclosures of which are incorporated herein by reference. Other suitable hydrophilic monomers will be apparent to one skilled in the art. For example, 2-hydroxyethylmethacrylate (HEMA) is a well-known hydrophilic monomer that may be used in admixture with the aforementioned hydrophilic monomers.

The monomer mixtures may also include a second device-forming monomer including a copolymerizable group and a reactive functional group. The copolyermizable group is preferably an ethylenically unsaturated group, such that this device-forming monomer copolymerizes with the hydrophilic device-forming monomer and any other device-forming monomers in the initial device-forming monomer mixture. Additionally, the second monomer can include a reactive functional group that reacts with a complementary reactive group of the silicone containing surfactant. In other words, after the device is formed by copolymerizing the device-forming monomer mixture, the reactive functional groups provided by the second device-forming monomers remain to react with a complementary reactive moiety of the silicone containing surfactant.

Preferred reactive groups of the second device-forming monomers include epoxide groups. Accordingly, preferred second device-forming monomers are those that include both an ethylenically unsaturated group (that permits the monomer to copolymerize with the hydrophilic device-forming monomer) and the epoxide group (that does not react with the hydrophilic device-forming monomer but remains to react with the silicone containing surfactant). Examples include glycidyl methacrylate, glycidyl acrylate, glycidyl vinylcarbonate, glycidyl vinylcarbamate, 4-vinyl-1-cyclohexene-1,2-epoxide and the like.

As mentioned, one preferred class of ophthalmic device substrate materials are silicone hydrogels. In this case, the initial device-forming monomer mixture further comprises a silicone-containing monomer. Applicable silicone-containing monomeric materials for use in the formation of silicone hydrogels are well known in the art and numerous examples are provided in U.S. Pat. Nos. 4,136,250; 4,153,641; 4,740,533; 5,034,461; 5,070,215; 5,260,000; 5,310,779; and 5,358,995. Specific examples of suitable materials for use herein include those disclosed in U.S. Pat. Nos. 5,310,779; 5,387,662; 5,449,729; 5,512,205; 5,610,252; 5,616,757; 5,708,094; 5,710,302; 5,714,557 and 5,908,906, the contents of which are incorporated by reference herein.

Representative examples of applicable silicon-containing monomers include bulky polysiloxanylalkyl(meth)acrylic monomers. The term "monomer" and like terms as used herein denote relatively low molecular weight compounds that are polymerizable by, for example, free radical polymerization, as well as higher molecular weight compounds also referred to as "prepolymers", "macromonomers", and related terms. The term "(meth)" as used herein denotes an optional methyl substituent. Accordingly, terms such as "(meth)acrylate" denotes either methacrylate or acrylate, and "(meth) acrylic acid" denotes either methacrylic acid or acrylic acid.

An example of a bulky polysiloxanylalkyl(meth)acrylic monomer is represented by the structure of Formula I:

(I)

wherein X denotes —O— or —NR—; each $R^1$ independently denotes hydrogen or methyl; each $R^2$ independently denotes a lower alkyl radical, phenyl radical or a group represented by wherein each $R^{2'}$ independently denotes a lower alkyl or phenyl radical; and h is 1 to 10.

Examples of bulky monomers are methacryloxypropyl tris (trimethyl-siloxy)silane or tris(trimethylsiloxy)silylpropyl methacrylate, sometimes referred to as TRIS and tris(trimethylsiloxy)silylpropyl vinyl carbamate, sometimes referred to as TRIS-VC and the like.

Such bulky monomers may be copolymerized with a silicone macromonomer, which is a poly(organosiloxane) capped with an unsaturated group at two or more ends of the molecule. U.S. Pat. No. 4,153,641 discloses, for example, various unsaturated groups such as acryloxy or methacryloxy groups.

Another class of representative silicone-containing monomers includes, but is not limited to, silicone-containing vinyl carbonate or vinyl carbamate monomers such as, for example, 1,3-bis[4-vinyloxycarbonyloxy)but-1-yl]tetramethyl-disiloxane; 3-(trimethylsilyl)propyl vinyl carbonate; 3-(vinyloxycarbonylthio)propyl-[tris(trimethylsiloxy)silane]; 3-[tris (trimethylsiloxy)silyl]propyl vinyl carbamate; 3-[tris (trimethylsiloxy)silyl]propyl allyl carbamate; 3-[tris (trimethylsiloxy)silyl]propyl vinyl carbonate; t-butyldimethylsiloxyethyl vinyl carbonate; trimethylsilylethyl vinyl carbonate; trimethylsilylmethyl vinyl carbonate and the like and mixtures thereof.

Another class of silicon-containing monomers includes polyurethane-polysiloxane macromonomers (also sometimes referred to as prepolymers), which may have hard-soft-hard blocks like traditional urethane elastomers. They may be end-capped with a hydrophilic monomer such as 2-hydroxyethyl methacrylate (HEMA). Examples of such silicone urethanes are disclosed in a variety or publications, including Lai, Yu-Chin, "The Role of Bulky Polysiloxanylalkyl Methacrylates in Polyurethane-Polysiloxane Hydrogels," Journal of Applied Polymer Science, Vol. 60, 1193-1199 (1996). PCT Published Application No. WO 96/31792 discloses examples of such monomers, which disclosure is hereby incorporated by reference in its entirety. Further examples of silicone urethane monomers are represented by Formulae II and III:

$$E(*D*A*D*G)_a*D*A*D*E'; \text{ or} \qquad (II)$$

$$E(*D*G*D*A)_a*D*A*D*E'; \text{ or} \qquad (III)$$

wherein:

D independently denotes an alkyl diradical, an alkyl cycloalkyl diradical, a cycloalkyl diradical, an aryl diradical or an alkylaryl diradical having 6 to about 30 carbon atoms;

G independently denotes an alkyl diradical, a cycloalkyl diradical, an alkyl cycloalkyl diradical, an aryl diradical or an alkylaryl diradical having 1 to about 40 carbon atoms and which may contain ether, thio or amine linkages in the main chain;

* denotes a urethane or ureido linkage;

a is at least 1;

A independently denotes a divalent polymeric radical of Formula IV:

(IV)

wherein each $R^s$ independently denotes an alkyl or fluoro-substituted alkyl group having 1 to about 10 carbon atoms which may contain ether linkages between the carbon atoms; m' is at least 1; and p is a number that provides a moiety weight of about 400 to about 10,000;

each of E and E' independently denotes a polymerizable unsaturated organic radical represented by Formula V:

(V)

wherein:
R³ is hydrogen or methyl;
R⁴ is hydrogen, an alkyl radical having 1 to 6 carbon atoms, or a —CO—Y—R⁶ radical wherein Y is —O—, —S— or —NH—;
R⁵ is a divalent alkylene radical having 1 to about 10 carbon atoms;
R⁶ is a alkyl radical having 1 to about 12 carbon atoms;
X denotes —CO— or —OCO—;
Z denotes —O— or —NH—;
Ar denotes an aromatic radical having about 6 to about 30 carbon atoms;
w is 0 to 6; x is 0 or 1; y is 0 or 1; and z is 0 or 1.

A preferred silicone-containing urethane monomer is represented by Formula VI:

wherein m is at least 1 and is preferably 3 or 4, a is at least 1 and preferably is 1, p is a number which provides a moiety weight of about 400 to about 10,000 and is preferably at least about 30, R⁷ is a diradical of a diisocyanate after removal of the isocyanate group, such as the diradical of isophorone diisocyanate, and each E" is a group represented by:

In another embodiment of the present invention, a silicone hydrogel material comprises (in bulk, that is, in the monomer mixture that is copolymerized) about 5 to about 50 percent, and preferably about 10 to about 25, by weight of one or more silicone macromonomers, about 5 to about 75 percent, and preferably about 30 to about 60 percent, by weight of one or more polysiloxanylalkyl (meth)acrylic monomers, and about 10 to about 50 percent, and preferably about 20 to about 40 percent, by weight of a hydrophilic monomer. In general, the silicone macromonomer is a poly(organosiloxane) capped with an unsaturated group at two or more ends of the molecule. In addition to the end groups in the above structural formulas, U.S. Pat. No. 4,153,641 discloses additional unsaturated groups, including acryloxy or methacryloxy. Fumarate-containing materials such as those disclosed in U.S. Pat. Nos. 5,310,779; 5,449,729 and 5,512,205 are also useful substrates in accordance with the invention. Preferably, the silane macromonomer is a silicon-containing vinyl carbonate or vinyl carbamate or a polyurethane-polysiloxane having one or more hard-soft-hard blocks and end-capped with a hydrophilic monomer.

The above silicone materials are merely exemplary, and other materials for use as substrates that can benefit by being packaged in the packaging solution according to the present invention and have been disclosed in various publications and are being continuously developed for use in contact lenses and other medical devices can also be used. For example, an ophthalmic lens for use herein can be a cationic lens such as a cationic contact lens or fluorinated silicone-containing monomers. Such monomers have been used in the formation of fluorosilicone as disclosed in, for example, U.S. Pat. Nos. 4,954,587; 5,010,141 and 5,079,319. The use of silicone-containing monomers having certain fluorinated side groups, i.e., —(CF₂)—H, have been found to improve compatibility between the hydrophilic and silicone-containing monomeric units. See, e.g., U.S. Pat. Nos. 5,321,108 and 5,387,662.

Ophthalmic devices such as contact lenses for application of the present invention can be manufactured employing various conventional techniques, to yield a shaped article having the desired posterior and anterior lens surfaces. In one embodiment, an ophthalmic device can be prepared by polymerizing the monomeric mixtures to form a product that can be subsequently formed into the appropriate shape by, for example, lathing, injection molding, compression molding, cutting and the like. For example, in producing contact lenses, the initial monomeric mixture may be polymerized in tubes to provide rod-shaped articles, which are then cut into buttons. The buttons may then be lathed into contact lenses.

Alternately, the ophthalmic devices may be cast directly in molds, e.g., polypropylene molds, from the monomeric mixtures, e.g., by spincasting and static casting methods. Spincasting methods are disclosed in U.S. Pat. Nos. 3,408,429 and 3,660,545, and static casting methods are disclosed in U.S. Pat. Nos. 4,113,224, 4,197,266, and 5,271,875. Spincasting methods involve charging the monomer mixture to a mold, and spinning the mold in a controlled manner while exposing the monomer mixture to a radiation source such as UV light. Static casting methods involve charging the monomeric mixture between two mold sections, one mold section shaped to form the anterior lens surface and the other mold section shaped to form the posterior lens surface, and curing the monomeric mixture while retained in the mold assembly to form a lens, for example, by free radical polymerization of the monomeric mixture. Examples of free radical reaction techniques to cure the lens material include thermal radiation, infrared radiation, electron beam radiation, gamma radiation, ultraviolet (UV) radiation, and the like; or combinations of such techniques may be used. U.S. Pat. No. 5,271,875 describes a static cast molding method that permits molding of a finished lens in a mold cavity defined by a posterior mold and an anterior mold. As an additional method, U.S. Pat. No. 4,555,732 discloses a process where an excess of a monomeric mixture is cured by spincasting in a mold to form a shaped article having an anterior lens surface and a relatively large thickness, and the posterior surface of the cured spincast article is subsequently lathed to provide a contact lens having the desired thickness and posterior lens surface.

Polymerization may be facilitated by exposing the mixture to heat and/or radiation, such as ultraviolet light, visible light, or high energy radiation. A polymerization initiator may be included in the mixture to facilitate the polymerization step. Representative examples of free radical thermal polymerization initiators include organic peroxides such as acetal peroxide, lauroyl peroxide, decanoyl peroxide, stearoyl peroxide, benzoyl peroxide, tertiarylbutyl peroxypivalate, peroxydicarbonate, and the like. Representative UV initiators are those known in the art and include benzoin methyl ether, benzoin ethyl ether, Darocure 1173, 1164, 2273, 1116, 2959, 3331 (EM Industries) and Irgacure 651 and 184 (Ciba-Geigy), and the like. Generally, the initiator will be employed in the monomeric mixture at a concentration of about 0.01 to 1 percent by weight of the total mixture.

After producing a lens having the desired final shape, it may be desirable to remove residual solvent from the lens before edge-finishing operations. This is because, typically, an organic diluent is included in the initial monomeric mixture in order to minimize phase separation of polymerized products produced by polymerization of the monomeric mixture and to lower the glass transition temperature of the reacting polymeric mixture, which allows for a more efficient curing process and ultimately results in a more uniformly polymerized product. Sufficient uniformity of the initial monomeric mixture and the polymerized product are of particular concern for silicone hydrogels, primarily due to the inclusion of silicone-containing monomers which may tend to separate from the hydrophilic comonomer. Suitable organic diluents include, for example, monohydric alcohols such as $C_6$-$C_{10}$ straight-chained aliphatic monohydric alcohols, e.g., n-hexanol and n-nonanol; diols such as ethylene glycol; polyols such as glycerin; ethers such as diethylene glycol monoethyl ether; ketones such as methyl ethyl ketone; esters such as methyl enanthate; and hydrocarbons such as toluene. Preferably, the organic diluent is sufficiently volatile to facilitate its removal from a cured article by evaporation at or near ambient pressure. Generally, the diluent is included at about 5 to about 60 percent by weight of the monomeric mixture, with about 10 to about 50 percent by weight being especially preferred.

The cured lens can then be subjected to solvent removal, which can be accomplished by evaporation at or near ambient pressure or under vacuum. An elevated temperature can be employed to shorten the time necessary to evaporate the diluent. The time, temperature and pressure conditions for the solvent removal step will vary depending on such factors as the volatility of the diluent and the specific monomeric components, as can be readily determined by one skilled in the art. According to a preferred embodiment, the temperature employed in the removal step is preferably at least about 50° C., for example, about 60° C. to about 80° C. A series of heating cycles in a linear oven under inert gas or vacuum may be used to optimize the efficiency of the solvent removal. The cured article after the diluent removal step should contain no more than twenty percent by weight of diluent, preferably no more than about 5 percent by weight or less.

Following removal of the organic diluent, the lens can then be subjected to mold release and optional machining operations. The machining step includes, for example, buffing or polishing a lens edge and/or surface. Generally, such machining processes may be performed before or after the article is released from a mold part. For example, the lens can be dry released from the mold by employing vacuum tweezers to lift the lens from the mold, after which the lens is transferred by means of mechanical tweezers to a second set of vacuum tweezers and placed against a rotating surface to smooth the surface or edges. The lens may then be turned over in order to machine the other side of the lens.

Next, the ophthalmic device such as a lens will be immersed in an aqueous packaging solution and stored in a packaging system according to the present invention. Generally, a packaging system for the storage of an ophthalmic device according to the present invention includes at least a sealed container containing one or more unused ophthalmic devices immersed in an aqueous packaging solution. Preferably, the sealed container is a hermetically sealed blister-pack, in which a concave well containing an ophthalmic device such as a contact lens is covered by a metal or plastic sheet adapted for peeling in order to open the blister-pack. The sealed container may be any suitable generally inert packaging material providing a reasonable degree of protection to the lens, preferably a plastic material such as polyalkylene, PVC, polyamide, and the like.

The aqueous packaging solution will contain at least a substantially water-soluble silicone-containing surfactant. The term "substantially water-soluble" as used herein shall be understood to mean a surfactant that dissolves in an aqueous medium resulting in an optically clear solution or provides a homogeneous dispersion when added to an aqueous medium. Preferably, the substantially water-soluble silicone-containing surfactant will dissolve in an aqueous medium to provide an optically clear solution. It is particularly undesirable to obtain a heterogeneous solution employing the silicone-containing surfactant according to the present invention, i.e., a solution containing a solid and a liquid phase. The term "surfactant" as used herein shall be understood to mean a surfactant containing one or more hydrophobic moieties and one or more hydrophilic moieties.

In one embodiment, a substantially water-soluble silicone-containing surfactant for use herein can be obtained from a polymerization product of a monomeric mixture containing at least a silicone-containing monomer and a hydrophilic comonomer. In general, the one or more hydrophobic moieties of the silicone-containing surfactant can be derived from a silicone-containing monomer while the one or more hydrophilic moieties can be derived from a hydrophilic monomer. It is believed that the hydrophobic moieties derived from a silicone-containing monomer will associate with the surface of an ophthalmic device such as a contact lens while the hydrophilic moieties derived from a hydrophilic monomer will provide enhanced lubricity to the device. In one embodiment, both of the silicone-containing monomers and hydrophilic monomers contain ethylenically unsaturated moieties.

Representative examples of applicable silicon-containing monomers include, but are not limited to, bulky polysiloxanylalkyl(meth)acrylic monomers as discussed hereinabove with respect to the monomers of Formula I:

(I)

wherein X denotes —O— or —NR— with R denoting hydrogen or a $C_1$-$C_4$ alkyl; each $R^1$ independently denotes hydrogen or methyl; each $R^2$ independently denotes a lower alkyl radical, phenyl radical or a group represented by wherein each $R^{2'}$ independently denotes a lower alkyl or phenyl radical; and h is 1 to 10, and the like.

Representative examples of other applicable silicon-containing monomers includes, but are not limited to, bulky polysiloxanylalkyl carbamate monomers as generally depicted in Formula Ia:

(Ia)

wherein X denotes —NR—; wherein R denotes hydrogen or a $C_1$-$C_4$ alkyl; $R^1$ denotes hydrogen or methyl; each $R^2$ independently denotes a lower alkyl radical, phenyl radical or a group represented by wherein each $R^{2'}$ independently denotes a lower alkyl or phenyl radical; and h is 1 to 10, and the like.

Examples of bulky monomers include methacryloxypropyl tris(trimethyl-siloxy)silane or tris(trimethylsiloxy)silylpropyl methacrylate (TRIS) and tris(trimethylsiloxy)silylpropyl vinyl carbamate (TRIS-VC) and the like.

Another class of silicon-containing monomers include polysiloxanes of general Formula VII:

(VII)

wherein each $R^8$ independently may be a monovalent hydrocarbon radical having 1 to about 18 carbon atoms which may have ether linkages between the carbon atoms including, by way of example, $C_1$-$C_4$ alkyl group; x>0; y>1; x+y=2 to 1000; and z is 1 to 20 and A is independently an activated unsaturated group, such as an ester or amide of an acrylic or a methacrylic acid, a styryl group, or is a group represented by the general formula:

wherein Y is —O—, —S— or —NH—. An example of a polysiloxane is an ethylenically unsaturated endcapped polydimethylsiloxane such as a methacrylate end-capped polydimethylsiloxane, and the like and mixtures thereof.

Yet another class of silicone-containing monomers include fluorinated silicone-containing monomers. Fluorinated siloxane-containing monomers useful in the present invention include those having at least one fluorinated side group, the side group having the general formula:

wherein z is 1 to 20; and D is an alkyl or alkylene group having 1 to about 10 carbon atoms and which may have ether linkages between the carbon atoms.

Polymeric materials useful in the method of the present invention may also be polymerized from monomer mixtures containing at least fluorinated siloxane-containing monomers having at least one fluorinated side group and having a moiety of the following general Formula VIII:

(VIII)

wherein D is an alkyl or alkylene group having 1 to about 10 carbon atoms and which may have ether linkages between carbon atoms; x>0; y>1; x+y=2 to 1000; and z is 1 to 20. A preferred material for use herein is a polymeric material prepared from monomer mixtures containing fluorinated siloxane-containing monomers having the following general Formula IX:

wherein $R^9$ is an alkyl or alkylene group having 1 to about 10 carbon atoms and which may have ether linkages between carbon atoms; each $R^{10}$ independently may be a monovalent hydrocarbon radical or a halogen substituted monovalent hydrocarbon radical having 1 to about 18 carbon atoms which may have ether linkages between carbon atoms; $x>0$; $y>1$; $x+y=2$ to 1000; and z is 1 to 20; and $R^{11}$ is independently a fluorinated side chain having the general formula:

wherein z is 1 to 20; D is an alkyl or alkylene group having 1 to about 10 carbon atoms and which may have ether linkages between carbon atoms; and A is independently an activated unsaturated group, such as an ester or amide of an acrylic or a methacrylic acid, a styryl group, or is a group represented by the general formula:

wherein Y is —O—, —S— or —NH—.

Preferably, the fluorinated side group is represented by the formula:

where z is 1 to 20. One preferred fluorinated siloxane-containing monomer, is prepared according to the following reaction scheme:

wherein y is 10, 25 and 40; x+y is 100; and z is 4 or 6.

In another embodiment, the fluorinated siloxane-containing monomers are fluorinated bulky polysiloxanylalkyl (meth)acrylate monomers represented by the general Formula X:

wherein A is an activated unsaturated group, such as an ester or amide of an acrylic or a methacrylic acid or a styryl group; $R^{12}$ is independently $CH_3$ or H; $R^{13}$ is an alkyl or alkylene group having 1 to about 10 carbon atoms and which may have ether linkages between the carbon atoms; D is independently an alkyl or alkylene group having 1 to about 10 carbon atoms and which may have ether linkages between carbon atoms; x is 1, 2 or 3; y is 0, 1, or 2; and x+y=3.

In another embodiment, fluorinated bulky polysiloxanylalkyl monomers for use herein can be represented by the general formula:

wherein $R^{14}$ is $CH_2$; and x is 1, 2 or 3; y is 0, 1 or 2; and x+y=3.

The silicone-containing monomers can be modified to contain one or more cationic groups. Suitable cationic groups that may be added to the silicone-containing prepolymer include, but are not limited to, an ammonium, phosphonium or sulphonium cationic-containing group as discussed hereinabove. Representative examples of such cationic groups can be those of the formula: $—X^1—N^+R^{15}{}_3$, $—X^1—P^+R^{16}{}_3$, $—X^1—S^+R^{16}{}_2$, or $—X^1$-Het$^+$, wherein $X^1$ is a substituted or unsubstituted alkylene group of 1 to about 12 carbon atoms, substituted or unsubstituted arylene group, substituted or unsubstituted alkylene arylene group, substituted or unsubstituted arylene alkylene group, substituted or unsubstituted alkylene aryl alkylene group, substituted or unsubstituted cycloalkylene group, substituted or unsubstituted alkylene cycloalkyl group, substituted or unsubstituted cycloalkyl alkylene group or substituted or unsubstituted alkylene cycloalkyl alkylene group; $R^{15}$ independently is hydrogen or a substituted or unsubstituted alkyl group of 1 to 4 carbon atoms, preferably methyl, or substituted or unsubstituted aryl, such as substituted or unsubstituted phenyl, or two of the $R^{15}$ groups together with the nitrogen atom to which they are attached form an aliphatic heterocyclic ring containing from 5 to 7 atoms, or three $R^{15}$ groups together with the nitrogen atom to which they are attached form a fused ring structure containing from 5 to 7 atoms in each ring; $R^{16}$ independently is $R^{15}$ or a group $—OR^{15}$, wherein $R^{15}$ is as defined herein; or Het is an aromatic nitrogen-, phosphorus- or sulphur-, preferably nitrogen-, containing ring such as, for example, pyridine.

Suitable hydrophilic monomers include, but are not limited to, (meth)acrylic substituted alcohols or polyols (e.g., glycols), such as 2-hydroxyethylmethacrylate, 2-hydroxyethylacrylate, glyceryl methacrylate, polyethyleneglycol methacrylate and the like; vinyl lactams, e.g., N-vinyl-2-pyrrolidone and the like; acrylamides, e.g., methacrylamide, N,N-dimethylacrylamide and the like, unsaturated carboxylic acids, e.g., (meth)acrylic acid and the like and mixtures thereof. Further examples of such hydrophilic monomers can be found in U.S. Pat. Nos. 4,153,641; 4,740,533; 5,034,461; and 5,070,215.

The relative ratio (wt. %) of silicone-containing monomer to total wt. % of comonomer mixture is from about 0.1 to about 50%, preferably from about 5 to about 30% and most preferably from about 10 to about 15%. As one skilled in the art will readily appreciate, when forming the substantially water-soluble silicone-containing surfactants according to the present invention, it may be necessary to employ minor amounts of silicone-containing monomers which are capable of being a cross-linking agent, e.g., a silicone-containing monomer of Formulae VII and IX, in the monomer mixture in order to provide a surfactant that is substantially water-soluble. A minor amount can vary widely according to the hydrophilic monomer in the monomer mixture and can be readily determined by one skilled in the art. Generally, a minor amount of the silicone-containing monomer in the monomer mixture can be less than about 25% by weight, based on the total weight of the mixture.

The silicone-containing surfactants can be obtained by copolymerizing the monomer mixture containing at least one or more of the foregoing silicone-containing monomers with one or more hydrophilic monomers by conventional techniques for polymerization, typically thermal or photochemical polymerization. For thermal polymerization a temperature from about 40° C. to about 120° C. is used. For photochemical polymerization, radiation such as gamma, U.V. or visible may be used. Typically U.V. radiation of wavelength about 200 to about 400 nm is used.

Alternatively, the polymerization products can be obtained by controlled free radical polymerization of the monomer mixture. Controlled free radical polymerization can be conducted by a variety of methods, such as with a TEMPO type polymerization, ATRP (atom transfer radical polymerization), GTP (Group transfer polymerization), and RAFT (Reversible addition-fragmentation chain transfer polymerization).

The polymerization is generally performed in a reaction medium Polymerization is generally performed in a reaction medium such as, for example, a solution or dispersion using a solvent, e.g., water, an alkanol containing from 1 to 12 carbon atoms such as methanol, ethanol, isopropanol, propan-2-ol, t-butanol, t-amyl alcohol, n-hexanol, nonanol and the like, cyclic ethers such as tetrahydrofuran and the like, aromatic hydrocarbons such as toluene and the like. Alternatively, a mixture of any of the above solvents may be used.

A polymerization initiator may be included in the mixture to facilitate the polymerization step. Representative free radical thermal polymerization initiators are usually peroxides or azo initiators such as, for example, acetal peroxide, lauroyl peroxide, decanoyl peroxide, stearoyl peroxide, benzoyl peroxide, tertiarylbutyl peroxypivalate, peroxydicarbonate, 2,2'-azo-bis(2-methylpropionitrile), benzoin methyl ether and the like and mixtures thereof. Representative UV initiators are those known in the field such as, for example, benzoin methyl ether, benzoin ethyl ether, Darocure 1173, 1164, 2273, 1116, 2959, 3331 (EM Industries) and Irgacure 651 and 184 (Ciba-Geigy), and the like and mixtures thereof. Generally, the initiator will be employed in the monomeric mixture at a concentration at about 0.1 to about 5 percent by weight of the total mixture.

Generally, polymerization can be carried out for about 1 to about 72 hours and preferably about 8 to about 48, and under an inert atmosphere of, for example, nitrogen or argon. If desired, the resulting polymer can be dried under vacuum, e.g., for about 5 to about 72 hours or left in an aqueous solution prior to use.

The weight average molecular weight of the resulting polymerization product may ordinarily range from about 100 to about 1,000,000 and preferably from about 250 to about 500,000. The resulting polymerization product can be in the form of random copolymers, block copolymers, graft copolymers and the like.

In another embodiment, a substantially water-soluble silicone-containing surfactant for use herein can be a silicone-containing prepolymer having at least one oxyalkylene moiety. The oxyalkylene moiety can be covalently bonded to the prepolymer as a terminal group or covalently bonded to the polymer backbone. In one embodiment, a substantially water-soluble silicone-containing surfactant will have at least one oxyalkylene unit of Formula XI:

(XI)

wherein $R^{17}$ and $R^{18}$ are independently hydrogen, methyl, an ether-containing group, a polyether-containing group, a $C_1$-$C_{20}$ ester group or a hydroxyl group, m is at least 1 and n is at least 1. The oxyalkylene units can be in block or random sequences.

Representative examples of ether or polyether containing groups for use herein include, by way of example, an alkyl ether, cycloalkyl ether, cycloalkylalkyl ether, cycloalkenyl ether, aryl ether, arylalkyl ether wherein the alkyl, cycloalkyl, cycloalkylalkyl, cycloalkenyl, aryl, and arylalkyl groups are as defined herein, e.g., alkylene oxides, poly(alkylene oxide)s such as ethylene oxide, propylene oxide, butylene oxide, poly(ethylene oxide)s, poly(ethylene glycol)s, poly(propylene oxide)s, poly(butylene oxide)s and mixtures or copolymers thereof, an ether or polyether group of the general formula —$R^{18}OR^{19}$, wherein $R^{18}$ is a bond, an alkyl, cycloalkyl or aryl group as defined herein and $R^{19}$ is an alkyl, cycloalkyl or aryl group as defined herein and the like.

Representative examples of alkyl groups for use herein include, by way of example, a straight or branched hydrocarbon chain radical containing carbon and hydrogen atoms of from 1 to about 4 carbon atoms with or without unsaturation, to the rest of the molecule, e.g., methyl, ethyl, n-propyl and the like.

Representative examples of cycloalkyl groups for use herein include, by way of example, a substituted or unsubstituted non-aromatic mono or multicyclic ring system of about 3 to about 30 carbon atoms such as, for example, cyclopropyl, cyclobutyl, cyclopentyl, cyclohexyl, perhydronapthyl, adamantyl and norbornyl groups bridged cyclic group or spirobicyclic groups, e.g., sprio-(4,4)-non-2-yl and the like, optionally containing one or more heteroatoms, e.g., O and N, and the like.

Representative examples of cycloalkylalkyl groups for use herein include, by way of example, a substituted or unsubstituted cyclic ring-containing radical containing from about 3 to about 30 carbon atoms directly attached to the alkyl group which are then attached to the main structure of the monomer at any carbon from the alkyl group that results in the creation of a stable structure such as, for example, cyclopropylmethyl, cyclobutylethyl, cyclopentylethyl and the like, wherein the cyclic ring can optionally contain one or more heteroatoms, e.g., O and N, and the like.

Representative examples of cycloalkenyl groups for use herein include, by way of example, a substituted or unsubstituted cyclic ring-containing radical containing from about 3 to about 30 carbon atoms with at least one carbon-carbon double bond such as, for example, cyclopropenyl, cyclobutenyl, cyclopentenyl and the like, wherein the cyclic ring can optionally contain one or more heteroatoms, e.g., O and N, and the like.

Representative examples of aryl groups for use herein include, by way of example, a substituted or unsubstituted monoaromatic or polyaromatic radical containing from about 5 to about 30 carbon atoms such as, for example, phenyl, naphthyl, tetrahydronapthyl, indenyl, biphenyl and the like, optionally containing one or more heteroatoms, e.g., O and N, and the like.

Representative examples of arylalkyl groups for use herein include, by way of example, a substituted or unsubstituted aryl group as defined above directly bonded to an alkyl group as defined above, e.g., —$CH_2C_6H_5$, —$C_2H_5C_6H_5$ and the like, wherein the aryl group can optionally contain one or more heteroatoms, e.g., O and N, and the like.

Representative examples of ester-containing groups for use herein include, by way of example, a carboxylic acid ester having one to 20 carbon atoms and the like.

Representative examples of hydroxyl-containing groups for use herein include, by way of example, —OH, a straight or branched $C_1$-$C_{12}$ hydrocarbon chain radical containing one or more hydroxyl groups bonded to a carbon atom on the hydrocarbon chain, and the like.

In another embodiment, a substantially water-soluble silicone-containing surfactant for use herein can be a silicone-containing prepolymer having at least one terminal oxyalkylene unit of the Formula XII:

(XII)

wherein $R^{17}$, $R^{18}$, n and m have the aforestated meanings and $R^{27}$ can be hydrogen, $C_1$-$C_{12}$ alkyl groups, and the like. In another embodiment, a silicone-containing prepolymer can have at least two side chains containing a terminal oxyalkylene unit of the Formula XII.

One class of a substantially water-soluble silicone-containing surfactant having one or more oxyalkylene radicals is of general Formula XIII:

(XIII)

wherein each $R^{28}$ is independently a straight or branched $C_1$-$C_{12}$ alkyl group, a $C_3$-$C_{30}$ cycloalkyl group, a $C_3$-$C_{30}$ cycloalkylalkyl group, a $C_3$-$C_{30}$ cycloalkenyl group, a $C_5$-$C_{30}$ aryl group, or a $C_5$-$C_{30}$ arylalkyl group as defined above; each $R^{28'}$ is independently one or more alkyleneoxide containing radicals as defined above; x is 0 or an integer of at least 1 and preferably from 1 to 200; and y is an integer of at least 1 and preferably from 1 to 200. Preferably, each $R^{28'}$ is independently an oxyalkylene containing radical of the formula:

—$R^{29}$—O-(EO)$_b$—(PO)$_c$—H wherein $R^{29}$ is independently an alkylene radical having 1 to 6 carbon atoms; EO is the ethylene oxide radical, preferably —($C_2H_4O$)—; PO is the propylene oxide radical, preferably —($CH_2CH(CH_3)O$)—; and each of b and c is independently 0 or an integer of at least 1, preferably b is at least 1.

In one embodiment, a substantially water-soluble silicone-containing surfactant for use herein can be a dimethylpolysiloxanes having at least one pendant side chain provided by the R' radical, i.e., dimethylpolysiloxanes wherein at least one methyl group attached to silicon is replaced with the oxyalkylene pendant side chain, including several materials available under the CTFA (Cosmetic, Toiletry and Fragrance Association, Inc.) name dimethicone copolyol. A representative example of a substantially water-soluble silicone-containing surfactant having one or more oxyalkylene radicals of general Formula XIII is as follows:

wherein $R^{28}$ and m have the aforestated meaning and p is an integer from 1 to 200. In one embodiment, m is 1. In another embodiment, m is 2.

Another class of a substantially water-soluble silicone-containing surfactants having one or more oxyalkylene radicals is of general Formula XIV:

wherein each $R^{28}$, y, n and m independently have the aforestated meanings and L is a linking group and independently can be a straight or branched $C_1$-$C_{12}$ alkyl group, a $C_3$-$C_{30}$ cycloalkyl group, a $C_3$-$C_{30}$ cycloalkylalkyl group, a $C_3$-$C_{30}$ cycloalkenyl group, a $C_5$-$C_{30}$ aryl group, or a $C_5$-$C_{30}$ arylalkyl group as defined above. Preferably, each oxyalkylene containing radical are EO or PO containing radicals. The oxyalkylene containing radicals can be random or block copolymers. In one embodiment, the silicone-containing prepolymers can be polydialkylsiloxane-polyethylene oxide block copolymers. In another embodiment, the silicone-containing surfactants can be polymethylsiloxane-polyethylene oxide block copolymers.

Another class of a substantially water-soluble silicone-containing surfactants having one or more oxyalkylene radicals is of general Formula XV:

wherein $R^2$, m and n have the aforestated meanings and h is from 1 to 10.

The a substantially water-soluble silicone-containing surfactants useful in the present invention may be further modified to be cationic. Suitable cationic groups include, but are not limited to, an ammonium, phosphonium or sulphonium cationic-containing group as discussed hereinabove.

Techniques that can be used for the preparation of suitable oxyalkylene side chain silicone-containing prepolymers useful in the present invention are well known and are not part of the present invention.

The amount of the substantially water-soluble silicone-containing surfactants employed in the packaging solution of the present invention is an amount effective to improve the surface properties of the ophthalmic device. Generally, the concentration of a substantially water-soluble silicone-containing surfactant present in the packaging solution of the packaging system according to the invention will range from about 0.01 to about 10% w/w, preferably from about 0.05 to about 5% w/w and most preferably from about 0.1 to about 1% w/w.

The packaging solutions according to the present invention are physiologically compatible. Specifically, the solution must be "ophthalmically safe" for use with a lens such as a contact lens, meaning that a contact lens treated with the solution is generally suitable and safe for direct placement on the eye without rinsing, that is, the solution is safe and comfortable for daily contact with the eye via a contact lens that has been wetted with the solution. An ophthalmically safe solution has a tonicity and pH that is compatible with the eye and includes materials, and amounts thereof, that are non-cytotoxic according to ISO standards and U.S. Food & Drug Administration (FDA) regulations.

The solution of the present invention should also be sterile in that the absence of microbial contaminants in the product prior to release must be statistically demonstrated to the degree necessary for such products. The liquid media useful in the present invention are selected to have no substantial detrimental effect on the lens being treated or cared for and to allow or even facilitate the present lens treatment or treatments. The liquid media are preferably aqueous-based. A particularly useful aqueous liquid medium is that derived from saline, for example, a conventional saline solution or a conventional buffered saline solution.

The pH of the present solutions should be maintained within the range of about 6 to about 9, and preferably about 6.5 to about 7.8. Suitable buffers may be added, such as boric acid, sodium borate, potassium citrate, citric acid, sodium bicarbonate, trishydroxymethylaminomethane and various mixed phosphate buffers (including combinations of $Na_2HPO_4$, $NaH_2PO_4$ and $KH_2PO_4$) and mixtures thereof. Generally, buffers will be used in amounts ranging from about 0.05 to about 2.5 percent by weight, and preferably from about 0.1 to about 1.5 percent by weight of the solution. The packaging solutions of this invention preferably contain a borate buffer, containing one or more of boric acid, sodium borate, potassium tetraborate, potassium metaborate or mixtures of the same.

Typically, the solutions of the present invention are also adjusted with tonicity agents, to approximate the osmotic pressure of normal lacrimal fluids which is equivalent to a 0.9 percent solution of sodium chloride or 2.5 percent of glycerol solution. The solutions are made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution which will cause stinging and eye irritation.

Examples of suitable tonicity adjusting agents include, but are not limited to, sodium and potassium chloride, dextrose, glycerin, calcium and magnesium chloride and the like and mixtures thereof. These agents are typically used individually in amounts ranging from about 0.01 to about 2.5% w/v and preferably from about 0.2 to about 1.5% w/v. Preferably, the tonicity agent will be employed in an amount to provide a final osmotic value of at least about 200 mOsm/kg, preferably from about 200 to about 400 mOsm/kg, more preferably from about 250 to about 350 mOsm/kg, and most preferably from about 280 to about 320 mOsm/kg.

If desired, one or more additional components can be included in the packaging solution. Such additional component or components are chosen to impart or provide at least one beneficial or desired property to the packaging solution. Such additional components may be selected from components which are conventionally used in one or more ophthalmic device care compositions. Examples of such additional components include cleaning agents, wetting agents, nutrient agents, sequestering agents, viscosity builders, contact lens conditioning agents, antioxidants, and the like and mixtures thereof. These additional components may each be included in the packaging solutions in an amount effective to impart or provide the beneficial or desired property to the packaging solutions. For example, such additional components may be included in the packaging solutions in amounts similar to the amounts of such components used in other, e.g., conventional, contact lens care products.

Useful sequestering agents include, but are not limited to, disodium ethylene diamine tetraacetate, alkali metal hexametaphosphate, citric acid, sodium citrate and the like and mixtures thereof.

Useful viscosity builders include, but are not limited to, hydroxyethyl cellulose, hydroxymethyl cellulose, polyvinyl pyrrolidone, polyvinyl alcohol and the like and mixtures thereof.

Useful antioxidants include, but are not limited to, sodium metabisulfite, sodium thiosulfate, N-acetylcysteine, butylated hydroxyanisole, butylated hydroxytoluene and the like and mixtures thereof.

The method of packaging and storing an ophthalmic device according to the present invention includes at least packaging an ophthalmic device immersed in the aqueous packaging solution described above. The method may include immersing the ophthalmic device in an aqueous packaging solution prior to delivery to the customer/wearer, directly following manufacture of the contact lens. Alternately, the packaging and storing in the solution according to the present invention may occur at an intermediate point before delivery to the ultimate customer (wearer) but following manufacture and transportation of the lens in a dry state, wherein the dry lens is hydrated by immersing the lens in the contact-lens packaging solution. Consequently, a package for delivery to a customer may include a sealed container containing one or more unused contact lenses immersed in an aqueous packaging solution according to the present invention.

In one embodiment, the steps leading to the present ophthalmic device packaging system includes (1) molding an ophthalmic device in a mold comprising at least a first and second mold portion, (2) hydrating and cleaning the device in a container comprising at least one of the mold portions, (3) introducing the packaging solution with the silicone-containing surfactant into the container with the device supported therein, and (4) sealing the container. Preferably, the method also includes the step of sterilizing the contents of the container. Sterilization may take place prior to, or most conveniently after, sealing of the container and may be effected by any suitable method known in the art, e.g., by autoclaving of the sealed container at temperatures of about 120° C. or higher.

The following examples are provided to enable one skilled in the art to practice the invention and are merely illustrative of the invention. The examples should not be read as limiting the scope of the invention as defined in the claims.

In the examples, the following abbreviations are used.

Tris-MA: tris(trimethylsiloxy)silylpropyl methacrylate

TRIS-VC: tris(trimethylsiloxy)silylpropyl vinyl carbamate

DMA: N,N-dimethylacrylamide

NVP: N-vinyl-2-pyrrolidone

MAA: methacrylic acid

THF: anhydrous tetrahydrofuran

Vazo™ 64: azo bis-isobutylnitrile (AIBN)

VPS-0501: A polydimethylsiloxane (PDMS) based macromolecular azo polymerization initiator (commercially available from Wako Pure Chemicals Industries, Ltd.) having a $M_W$ of 30,000 to 50,000 with the molecular weight of the PDMS segments between the azo groups of 5,000. Therefore, it is expected that the reaction product produces diblock and triblock copolymers with the $M_W$ of the PDMS chain being approximately 5000.

Examples 1

Preparation of Tris-MA/NVP Copolymer

The amounts for Tris-MA and NVP employed in this example are set forth below in Table 1:

TABLE 1

| Examples | Mol Ratio Tris-MA:NVP | Tris-MA (grams) | NVP (grams) |
|---|---|---|---|
| Example 1 | 1:99 | 0.370 | 9.630 |

Into a 100 mL round bottom flask was added Tris-MA and NVP in the amounts set forth in Table 1. THF (30 mL) and 3 mL of a 10 mg/mL stock solution of Vazo™ 64 dissolved in THF were added to the reaction flask. The reaction mixture was sparged with nitrogen gas for 30 minutes and then heated to 64° C. in an oil bath under a blanket of nitrogen for 48 hours. The reaction mixture was allowed to cool and then was precipitated into cold diethylether (500 mL). The copolymer was isolated by filtration and dried in a vacuum oven at 45° C. overnight.

Examples 2A and 2B

Preparation of TRIS-MA/DMA Copolymers

The amounts for Tris-MA and DMA for Examples 2A and 2B are set forth below in Table 2:

TABLE 2

| Examples | Mol Ratio Tris-MA:DMA | Tris-MA (grams) | DMA (grams) |
| --- | --- | --- | --- |
| Example 2A | 1:99 | 0.413 | 9.587 |
| Example 2B | 2:98 | 0.801 | 9.199 |

Into a 100 mL round bottom flask was added Tris-MA and DMA in the amounts set forth in Table 2. THF (30 mL) and 3 mL of a 10 mg/mL stock solution of Vazo™ 64 dissolved in THF were added to the reaction flask. The reaction mixture was sparged with nitrogen gas for 0.5 hour and then heated to 64° C. in an oil bath under a blanket of nitrogen for 48 hours. The reaction mixture was allowed to cool and then was precipitated into cold hexane (500 mL). The copolymer was isolated by filtration and dried in a vacuum oven at 45° C. overnight.

Examples 3A-3C

Preparation of Tris-MA/MAA Copolymers

The amounts for Tris-MA and MAA for Examples 3A-3D are set forth below in Table 3:

TABLE 3

| Examples | Mol Ratio Tris-MA:MAA | Tris-MA (grams) | MAA (grams) |
| --- | --- | --- | --- |
| Example 3A | 1:99 | 0.473 | 9.527 |
| Example 3B | 2:98 | 0.911 | 9.089 |
| Example 3C | 5:95 | 2.054 | 7.946 |

Into a 100 mL round bottom flask was added Tris-MA and MAA in the amounts set forth in Table 3. THF (30 mL) and 3 mL of a 10 mg/mL stock solution of Vazo™ 64 dissolved in methanol were added to the reaction flask. The reaction mixture was sparged with nitrogen gas for 0.5 hour and then heated to 64° C. in an oil bath under a blanket of nitrogen for 48 hours. The reaction mixture was allowed to cool and then was precipitated into cold diethyl ether (500 mL). The copolymer was isolated by filtration. The polymer was dried in a vacuum oven at 45° C. overnight.

Examples 4A-4D

Preparation of Tris-VC/NVP Copolymers

The amounts for Tris-VC and NVP for Examples 4A-4D are set forth below in Table 4:

TABLE 4

| Examples | Mol Ratio Tri-VC:NVP | TRIS-VC (grams) | NVP (grams) |
| --- | --- | --- | --- |
| Example 4A | 1:99 | 0.741 | 19.259 |
| Example 4B | 2:98 | 1.442 | 18.558 |
| Example 4C | 5:95 | 3.339 | 16.661 |
| Example 4D | 10:90 | 5.946 | 14.054 |

Into a 500 mL round bottom flask was added Tris-VC and NVP in the amounts set forth in Table 4. Methanol (100 mL) and 6 mL of a 10 mg/mL stock solution of Vazo™ 64 dissolved in methanol were added to the reaction flask. The reaction mixture was sparged with nitrogen gas for 30 minutes and heated to 64° C. in an oil bath under a blanket of nitrogen for 48 hours. The reaction mixture was allowed to cool and then was precipitated into cold diethyl ether (500 mL). The copolymer was isolated by filtration and dried in a vacuum oven at 45° C. overnight.

Examples 5A-5D

Preparation of PDMS Block Copolymers

The ingredients in amounts for these examples are set forth in Table 5 below:

TABLE 5

| Examples | Desired DP* of Vinyl Monomer | Macroinitiator VPS-0501 (g) | NVP or DMA (g) |
| --- | --- | --- | --- |
| Example 5A | 150 | 2.13 | 7.10 (NVP) |
| Example 5B | 150 | 2.21 | 6.57 (DMA) |
| Example 5C | 300 | 3.42 | 22.80 (NVP) |
| Example 5D | 300 | 2.98 | 17.72 (DMA) |

*DP in the above table is defined as the number of repeating units of the monomer expected by polymerization on the end of the PDMS macroinitiator.

VPS-0501 macroinitiator was added to a round bottom flask along with 25 mL of THF. Next, NVP or DMA was added to the flask in the amount set forth in Table 5 and the reaction mixture was sparged with nitrogen gas for 30 minutes. The reaction mixture was then heated in an oil bath under a blanket of nitrogen for 24 hours. The reaction was stopped and the reaction product was precipitated into cold diethylether and isolated by filtration (Examples 5C and 5D) or by decanting off the non-solvent after the polymer was allowed to settle (Examples 5A and 5B). The product was then dried in a vacuum oven at 45° C. overnight.

Example 6

An aqueous packaging solution containing 1% by weight of the silicone-containing surfactant of Example 1 dissolved in a borate buffered saline at a pH of 7.2 was placed in a polypropylene blister package. Next, a balafilcon A contact lens (a commercially available group III extended wear contact lenses from Bausch & Lomb Incorporated of Rochester, N.Y., sold under the trade name Purevision®, made of a silicone hydrogel material and having an anionic charge and approximately 38% water) was immersed in the aqueous packaging solution in the polypropylene blister package. The package was sealed with foil lidstock and then autoclaved for 30 minutes at 121° C.

Example 7

An aqueous packaging solution containing 1% by weight of the silicone-containing surfactant of Example 2A dissolved in a borate buffered saline at a pH of 7.2 was placed in a polypropylene blister package. Next, a balafilcon A contact lens (a commercially available group III extended wear contact lenses from Bausch & Lomb Incorporated of Rochester, N.Y., sold under the trade name Purevision®, made of a silicone hydrogel material and having an anionic charge and approximately 38% water) was immersed in the aqueous packaging solution in the polypropylene blister package. The package was sealed with foil lidstock and then autoclaved for 30 minutes at 121° C.

Example 8

An aqueous packaging solution containing 1% by weight of the silicone-containing surfactant of Example 2B dissolved in a borate buffered saline at a pH of 7.2 was placed in a polypropylene blister package. Next, a balafilcon A contact lens (a commercially available group III extended wear contact lenses from Bausch & Lomb Incorporated of Rochester, N.Y., sold under the trade name Purevision®, made of a silicone hydrogel material and having an anionic charge and approximately 38% water) was immersed in the aqueous packaging solution in the polypropylene blister package. The package was sealed with foil lidstock and then autoclaved for 30 minutes at 121° C.

Example 9

An aqueous packaging solution containing 1% by weight of the silicone-containing surfactant of Example 3A dissolved in a borate buffered saline at a pH of 7.2 was placed in a polypropylene blister package. Next, a balafilcon A contact lens (a commercially available group III extended wear contact lenses from Bausch & Lomb Incorporated of Rochester, N.Y., sold under the trade name Purevision®, made of a silicone hydrogel material and having an anionic charge and approximately 38% water) was immersed in the aqueous packaging solution in the polypropylene blister package. The package was sealed with foil lidstock and then autoclaved for 30 minutes at 121° C.

Example 10

An aqueous packaging solution containing 1% by weight of the silicone-containing surfactant of Example 3B dissolved in a borate buffered saline at a pH of 7.2 was placed in a polypropylene blister package. Next, a balafilcon A contact lens (a commercially available group III extended wear contact lenses from Bausch & Lomb Incorporated of Rochester, N.Y., sold under the trade name Purevision®, made of a silicone hydrogel material and having an anionic charge and approximately 38% water) was immersed in the aqueous packaging solution in the polypropylene blister package. The package was sealed with foil lidstock and then autoclaved for 30 minutes at 121° C.

Example 11

An aqueous packaging solution containing 1% by weight of the silicone-containing surfactant of Example 3C dissolved in a borate buffered saline at a pH of 7.2 was placed in a polypropylene blister package. Next, a balafilcon A contact lens (a commercially available group III extended wear contact lenses from Bausch & Lomb Incorporated of Rochester, N.Y., sold under the trade name Purevision®, made of a silicone hydrogel material and having an anionic charge and approximately 38% water) was immersed in the aqueous packaging solution in the polypropylene blister package. The package was sealed with foil lidstock and then autoclaved for 30 minutes at 121° C.

Example 12

An aqueous packaging solution containing 1% by weight of the silicone-containing surfactant of Example 4A dissolved in a borate buffered saline at a pH of 7.2 was placed in a polypropylene blister package. Next, a balafilcon A contact lens (a commercially available group III extended wear contact lenses from Bausch & Lomb Incorporated of Rochester, N.Y., sold under the trade name Purevision®, made of a silicone hydrogel material and having an anionic charge and approximately 38% water) was immersed in the aqueous packaging solution in the polypropylene blister package. The package was sealed with foil lidstock and then autoclaved for 30 minutes at 121° C.

Example 13

An aqueous packaging solution containing 1% by weight of the silicone-containing surfactant of Example 4B dissolved in a borate buffered saline at a pH of 7.2 was placed in a polypropylene blister package. Next, a balafilcon A contact lens (a commercially available group III extended wear contact lenses from Bausch & Lomb Incorporated of Rochester, N.Y., sold under the trade name Purevision®, made of a silicone hydrogel material and having an anionic charge and approximately 38% water) was immersed in the aqueous packaging solution in the polypropylene blister package. The package was sealed with foil lidstock and then autoclaved for 30 minutes at 121° C.

Example 14

An aqueous packaging solution containing 1% by weight of the silicone-containing surfactant of Example 4C dissolved in a borate buffered saline at a pH of 7.2 was placed in a polypropylene blister package. Next, a balafilcon A contact lens (a commercially available group III extended wear contact lenses from Bausch & Lomb Incorporated of Rochester, N.Y., sold under the trade name Purevision®, made of a silicone hydrogel material and having an anionic charge and approximately 38% water) was immersed in the aqueous packaging solution in the polypropylene blister package. The package was sealed with foil lidstock and then autoclaved for 30 minutes at 121° C.

Example 15

An aqueous packaging solution containing 1% by weight of the silicone-containing surfactant of Example 4D dissolved in a borate buffered saline at a pH of 7.2 was placed in a polypropylene blister package. Next, a balafilcon A contact lens (a commercially available group III extended wear contact lenses from Bausch & Lomb Incorporated of Rochester, N.Y., sold under the trade name Purevision®, made of a silicone hydrogel material and having an anionic charge and approximately 38% water) was immersed in the aqueous packaging solution in the polypropylene blister package. The package was sealed with foil lidstock and then autoclaved for 30 minutes at 121° C.

Example 16

An aqueous packaging solution containing 2% by weight of the silicone-containing surfactant of Example 4B dissolved in a borate buffered saline at a pH of 7.2 was placed in a polypropylene blister package. Next, a balafilcon A contact lens (a commercially available group III extended wear contact lenses from Bausch & Lomb Incorporated of Rochester, N.Y., sold under the trade name Purevision®, made of a silicone hydrogel material and having an anionic charge and approximately 38% water) was immersed in the aqueous packaging solution in the polypropylene blister package. The package was sealed with foil lidstock and then autoclaved for 30 minutes at 121° C.

Example 17

An aqueous packaging solution containing 2% by weight of the silicone-containing surfactant of Example 4C dissolved in a borate buffered saline at a pH of 7.2 was placed in a polypropylene blister package. Next, a balafilcon A contact lens (a commercially available group III extended wear contact lenses from Bausch & Lomb Incorporated of Rochester, N.Y., sold under the trade name Purevision®, made of a silicone hydrogel material and having an anionic charge and approximately 38% water) was immersed in the aqueous packaging solution in the polypropylene blister package. The package was sealed with foil lidstock and then autoclaved for 30 minutes at 121° C.

Example 18

An aqueous packaging solution containing 1% by weight of the silicone-containing surfactant commercially available as Dow Corning® 193 Fluid dissolved in a borate buffered saline at a pH of 7.2 was placed in a polypropylene blister package. Next, a balafilcon A contact lens (a commercially available group III extended wear contact lenses from Bausch & Lomb Incorporated of Rochester, N.Y., sold under the trade name Purevision®, made of a silicone hydrogel material and having an anionic charge and approximately 38% water) was immersed in the aqueous packaging solution in the polypropylene blister package. The package was sealed with foil lidstock and then autoclaved for 30 minutes at 121° C.

Example 19

An aqueous packaging solution within the scope of the present invention containing 1% by weight of the silicone-containing surfactant ((40% hydroxyethyleneoxy-propylmethylsiloxane)-(dimethylsiloxane) copolymer) commercially available as Gelest CMC-626 dissolved in a borate buffered saline at a pH of 7.2 was placed in a polypropylene blister package. Next, a balafilcon A contact lens (a commercially available group III extended wear contact lenses from Bausch & Lomb Incorporated of Rochester, N.Y., sold under the trade name Purevision®, made of a silicone hydrogel material and having an anionic charge and approximately 38% water) was immersed in the aqueous packaging solution in the polypropylene blister package. The package was sealed with foil lidstock and then autoclaved for 30 minutes at 121° C.

Example 20

Figure 1:
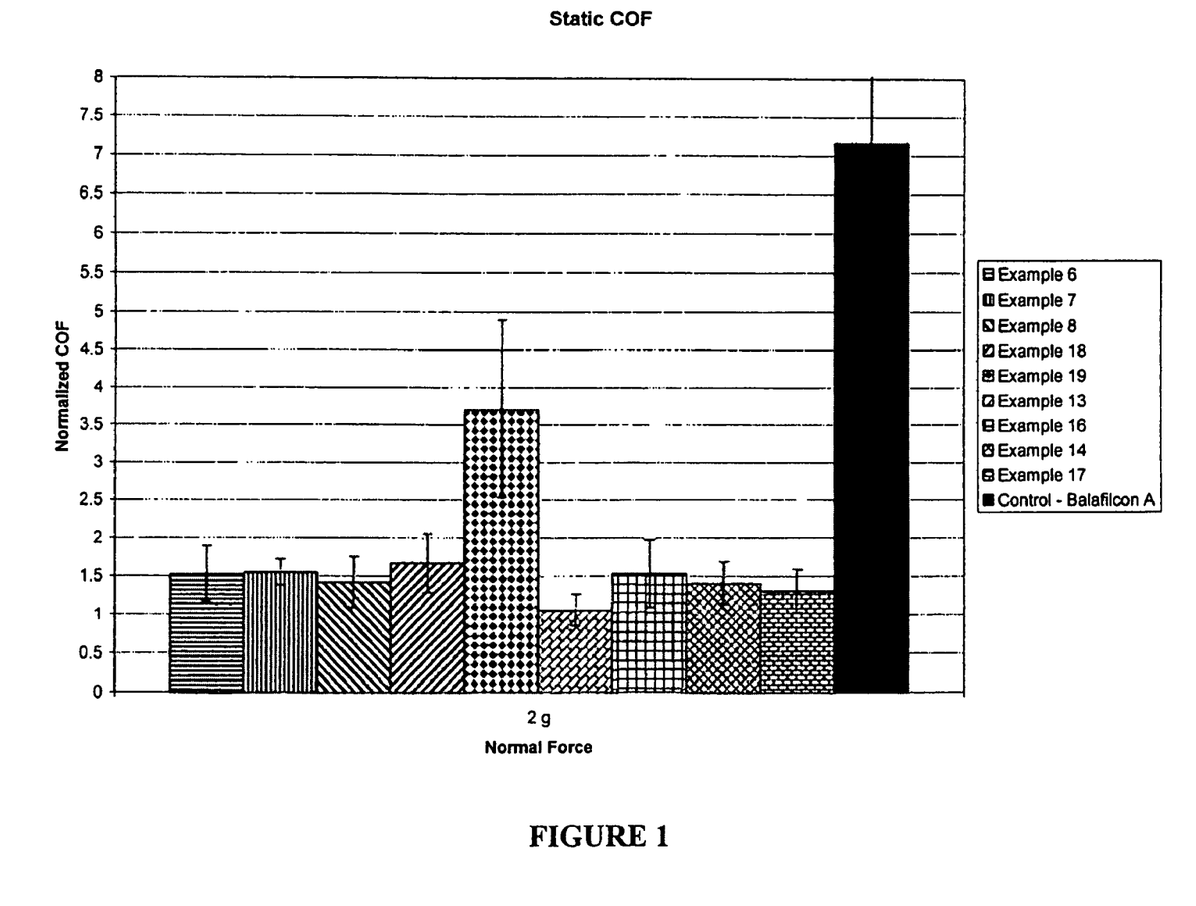
FIG. 1 is a bar graph showing normalized coefficient of friction for surface modified contact lenses according to the present invention.
Figure 2:
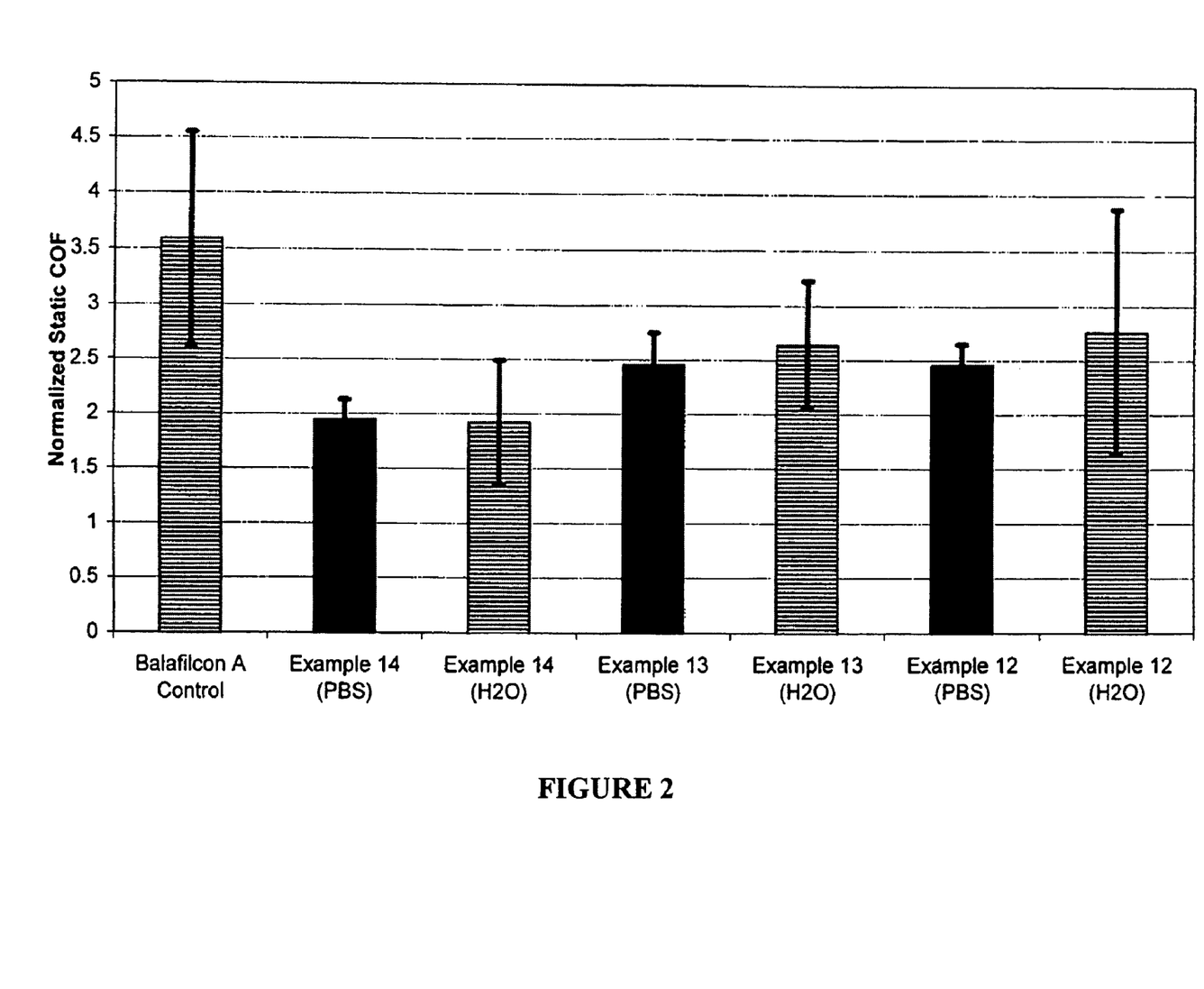
FIG. 2 is a bar graph showing normalized coefficient of friction for surface modified contact lenses according to the present invention.

Tribological testing was performed on the samples of Examples 6, 7, 8, 12, 13, 14, 16, 17, 18 and 19 using a CETR Model UMT-2 micro-tribometer. Each of the sealed polypropylene blister packages according to Examples 6, 7, 8, 12, 13, 14, 16, 17, 18 and 19 were unsealed and the contact lens was removed from the solution in the package. Each lens was immediately mounted and tested in 1 mL phosphate borate saline (PBS). The lens was clamped on an HDPE holder that initially mates with the posterior side of the lens. A poly (propylene) clamping ring was then used to hold the edge region of the lens. Once the lens was mounted in the holder the assembly was placed in a stationary clamping device within the micro-tribometer. A polished stainless steel disc containing 1 mL of a phosphate buffered saline (PBS) was then brought into contact with the lens and normal force was adjusted to 2 grams over the course of the run for the frictional measurements. After the load equilibrated for 5 seconds the stainless steel disc was rotated at a velocity of 12 cm/sec for a duration of 20 seconds in both the forward and reverse directions and the peak (static) and average (kinetic) COF values were recorded. Each value represents the average of 7 to 8 lenses. All data was normalized to the average values obtained at 2 g force from the lens holder in the absence of a lens tested in PBS. Statistical analyses were carried out using Design-Expert software. Statistical comparisons were made using standardized T-tests. The results from this study are shown in FIGS. 1 and 2.

Tribology is the study of how two surfaces interact with each other when in relative motion. One aspect of tribology that may be of importance to contact lenses is friction. Friction is a measure of a material's resistance to lateral motion when placed against a specific substrate. The relative friction between two surfaces may be described in terms of a coefficient of friction (COF), which is defined as the ratio of the lateral force ($F_x$) that is required to initiate and then sustain movement to the normal force ($F_N$). Further, there are two friction coefficients that may be considered, the peak (or static) and average (or kinetic). The static COF is a measure of how much $F_x$ is needed to initiate relative motion of two surfaces and is typically the larger of the two values. Practically, for contact lenses, the static COF is related to the amount of force needed to start a blink cycle or for the lens to begin moving over the cornea. The kinetic COF is a measure of how much lateral force is needed to sustain movement at a particular velocity averaged over a finite period of time. This value is related to the amount of force required to sustain the blink over the course of the entire cycle and the ease of motion of the lens on the cornea (which may be further related to how much the lens moves on the cornea).

Example 21

Each of the sealed polypropylene blister packages according to Examples 8, 12, 13, 14, 16, and 17 were unsealed and the lenses soaked in the packaging solution were removed from the packaging solution and rubbed between the thumb and index finger to assess lubricity. The surface modified lenses of the present invention, i.e., the lenses treated according to Examples 8, 12, 13, 14, 16, and 17 felt more lubricious than the control lens. The control lens was a balafilcon A contact lens immersed in a borate buffer saline polypropylene blister package. The package containing the control lens was sealed with foil lidstock and then autoclaved for 30 minutes at 121° C.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A method of preparing a package comprising a storable, sterile ophthalmic device, the method comprising:
    (a) immersing an ophthalmic device in an aqueous packaging solution comprising a substantially water-soluble silicone-containing surfactant, wherein the solution has an osmolality of at least about 200 mOsm/kg and a pH in the range of about 6 to about 9;

(b) packaging the solution and the device in a manner preventing contamination of the device by microorganisms; and (c) sterilizing the packaged solution and device, wherein the substantially water-soluble silicone-containing surfactant is a polymerization product of a monomeric mixture comprising one or more silicone-containing monomers having at least one ethylenically unsaturated terminal group and one or more ethylenically unsaturated, hydrophilic comonomers.

2. The method of claim 1, wherein the ophthalmic device is a contact lens.

3. The method of claim 1, wherein the ophthalmic device is a silicone hydrogel contact lens.

4. The method of claim 1, wherein the substantially water-soluble silicone-containing surfactant comprises one or more hydrophobic moieties and one or more hydrophilic moieties.

5. The method of claim 1, wherein the silicon-containing monomer is a polysiloxanylalkyl(meth)acrylic monomer or a polysiloxanylalkyl carbamate monomer.

6. The method of claim 1, wherein the hydrophilic comonomer is selected from the group consisting of an unsaturated carboxylic acid, (meth)acrylic substituted alcohol, vinyl lactam, (meth)acrylamide and combinations thereof.

7. The method of claim 5, wherein the hydrophilic comonomer is selected from the group consisting of 2-hydroxyethylmethacrylate, 2-hydroxyethylacrylate, glyceryl methacrylate, N-vinyl pyrrolidone, N-vinyl-N-methyl acetamide, N,N-dimethyl methacrylamide, N,N-dimethylacrylamide, acrylic acid, methacrylic acid and combinations thereof.

8. The method of claim 1, wherein the concentration of the substantially water-soluble silicone-containing surfactant in the aqueous packaging solution is about 0.01 to about 10% w/w.

9. The method of claim 1, wherein the solution does not contain an effective disinfecting amount of a disinfecting agent.

10. The method of claim 1, wherein the solution does not contain a germicide compound.

11. A packaging system for the storage of an ophthalmic device comprising a sealed container containing one or more unused ophthalmic devices immersed in an aqueous packaging solution comprising a substantially water-soluble silicone-containing surfactant, wherein the solution has an osmolality of at least about 200 mOsm/kg, a pH of about 6 to about 9 and is heat sterilized, wherein the substantially water-soluble silicone-containing surfactant is a polymerization product of a monomeric mixture comprising one or more silicone-containing monomers having at least one ethylenically unsaturated terminal group and one or more ethylenically unsaturated, hydrophilic comonomers.

12. The packaging system of claim 11, wherein the ophthalmic device is a contact lens.

13. The packaging system of claim 11, wherein the substantially water-soluble silicone-containing surfactant comprises one or more hydrophobic moieties and one or more hydrophilic moieties.

14. The packaging system of claim 11, wherein the silicon-containing monomer is a polysiloxanylalkyl(meth)acrylic monomer or a polysiloxanylalkyl carbamate monomer.

15. The packaging system of claim 14, wherein the hydrophilic comonomer is selected from the group consisting of 2-hydroxyethylmethacrylate, 2-hydroxyethylacrylate, glyceryl methacrylate, N-vinyl pyrrolidone, N-vinyl-N-methyl acetamide, N,N-dimethyl methacrylamide, N,N-dimethylacrylamide, acrylic acid, methacrylic acid and combinations thereof.

16. The packaging system of claim 11, wherein the hydrophilic comonomer is selected from the group consisting of an unsaturated carboxylic acid, (meth)acrylic substituted alcohol, vinyl lactam, (meth)acrylamide and combinations thereof.

17. The packaging system of claim 11, wherein the concentration of the substantially water-soluble silicone-containing surfactant in the aqueous packaging solution is about 0.01 to about 10% w/w.

18. The packaging system of claim 11, wherein the solution does not contain an effective disinfecting amount of a disinfecting agent.

19. The packaging system of claim 11, wherein the solution does not contain a germicide compound.

20. The packaging system of claim 11, wherein the package is heat sterilized subsequent to sealing of the package.

* * * * *